United States Patent [19]
Bremer

[11] Patent Number: 5,697,895
[45] Date of Patent: Dec. 16, 1997

[54] HALO RING WITH LONGITUDINALLY AND ANGULARLY ADJUSTABLE PINS

[76] Inventor: Ross L. Bremer, 1502 Beach Ave., Atlantic Beach, Fla. 32233

[21] Appl. No.: 648,247

[22] Filed: May 15, 1996

[51] Int. Cl.⁶ ..................................................... A61F 5/00
[52] U.S. Cl. ........................... 602/37; 602/36; 602/17; 128/DIG. 23
[58] Field of Search ............... 128/DIG. 23; 602/17–19, 602/33, 36–37, 40; 606/56, 59

[56] References Cited

U.S. PATENT DOCUMENTS

| | | | |
|---|---|---|---|
| 2,391,693 | 12/1945 | Ettinger | 606/59 |
| 2,851,031 | 9/1958 | Ciampa | 602/17 X |
| 3,072,118 | 1/1963 | Standerwick et al. | |
| 4,535,763 | 8/1985 | Jaquet | 606/56 |
| 4,541,421 | 9/1985 | Iverson et al. | 602/18 |
| 4,620,530 | 11/1986 | Lanier et al. | 602/17 X |
| 4,648,388 | 3/1987 | Steffee | 606/59 X |
| 4,890,631 | 1/1990 | Hardy | 606/59 |
| 5,062,415 | 11/1991 | Weatherby et al. | |
| 5,156,588 | 10/1992 | Marcune et al. | |
| 5,171,296 | 12/1992 | Herman | |
| 5,203,765 | 4/1993 | Friddle, Jr. | 602/18 |
| 5,261,873 | 11/1993 | Bremer et al. | 602/36 X |
| 5,380,325 | 1/1995 | Lahille et al. | 606/59 X |
| 5,456,266 | 10/1995 | Brown | |
| 5,527,309 | 6/1996 | Shelton | 606/59 X |
| 5,537,704 | 7/1996 | Dinkler | 602/33 X |

*Primary Examiner*—Richard J. Apley
*Assistant Examiner*—Denise Pothier
*Attorney, Agent, or Firm*—Nixon & Vanderhye

[57] ABSTRACT

The halo ring comprises a generally elliptical ring interrupted at one end and having a circular cross-section. Split ring clamps are provided along the ring, each clamp having a set screw for temporarily adjusting the ring in a selected longitudinal along and angular position about the halo ring. Attachment clamps in the form of split rings are also provided the halo ring body for securing the halo ring to a support structure. By threading pins through the pin clamps into the individual's skull and employing lock nuts, the pin clamps can be finally secured to the halo ring body.

16 Claims, 3 Drawing Sheets

HALO RING WITH LONGITUDINALLY AND ANGULARLY ADJUSTABLE PINS

TECHNICAL FIELD

The present invention relates to halo rings for use by patients with cervical or spinal injuries for immobilizing the neck of the patient to promote healing and particularly relates to a halo ring having pin clamps adjustable longitudinally along and angularly about the halo ring body for longitudinal and angular orientation of the pins relative to the ring and to the patient's head enabling a substantially 90° interface with the patient's head at all attachment locations.

BACKGROUND

Halo rings used in conjunction with halo superstructure support systems, for example, halo vests, are orthopedic devices normally applied by a medical practitioner such as an orthopedic or neurological surgeon to a patient having cervical or spinal injuries for immobilizing the patients to promote healing, which often takes many months. Typical halo rings comprise a generally arcuate ring or body which peripherally surrounds the front and side portions of a patient's head. Certain specific types of halo rings also include an angled arcuate piece bridging rear ends of the ring and extending toward the rear upper portion of the patient's head. Holes are typically formed through the halo ring at intervals therealong for receiving threaded skull pins. The locations and directions of the axes of the holes through the halo ring determine the angular orientation of the skull pins. The skull pins are thus fixed in location about and in angular orientation relative to the ring, the axes of the pins being determined by the axes of the preformed holes. It is highly desirable to connect the skull pins with the individual's skull at an interface where the pins project from the skull at right angles or as close to right angles as possible in both lateral and vertical directions. However, with the fixed location of the holes, as well as the fixed axes of the holes in conventional halo rings, the selection of the location and orientation of the pins in the ring and relative to the skull are severely limited. For example, where the shape of the halo ring body is generally semi-circular, it will be appreciated that the pins may typically extend along a radius of the semi-circular ring and in a plane defined by the semi-circular ring. Oftentimes, the traditional fixed pin location and orientation in the halo ring body does not permit an optimum fit between the halo ring and the patient's skull. While custom halo rings may be individualized for particular patients, this is very costly. There has thus developed a need for a halo ring wherein the pins can be selectively adjusted to change their location and angularity about the halo ring body.

DISCLOSURE OF THE INVENTION

According to the present invention, there is provided a novel and improved halo ring having skull attachment pins which can be adjusted in location along the ring and angularity relative to the halo ring body, i.e., relative to a plane containing the halo ring body and hence about the patient's skull. Additionally, the present invention provides for above and/or below equator pin location. Thus, according to the present invention, the pins are substantially infinitely adjustable along the length of and in angular orientation relative to the halo body.

To accomplish the foregoing, the present invention provides a halo ring body which generally conforms to the periphery of a patient's skull and, in a preferred form, terminates in discrete ends spaced one from the other. The halo body in plan view is in the form of an ellipse with one end removed although it will be appreciated that other shapes in plan view are possible, for example, an interrupted circle or an arcuate shape specific to an individual's head. Instead of holes formed at fixed locations along the ring and having axes generally along radii of the ring as in the prior art, the present invention provides for a plurality of pin clamps which are slidable along the ring into selected meridian locations about the halo ring and selected angular positions relative to the ring. Each pin clamp may comprise a split circular clamp having a pair of flanges adjacent the free ends mounting aligned holes, one of which is threaded to receive a halo pin. Located about the pin clamp is a temporary securing or retention element for temporarily securing the pin clamp in an adjusted position relative to the halo body. The retention element may comprise a set screw for temporarily securing the clamp to the halo ring in its adjusted positions. The halo pin may have a head and a locking nut so that when the pin is received through the bores of the clamp, the pin may be extended to the patient's skull and simultaneously locked into place to the halo ring body.

To enable the pin clamp for adjustable location along the halo ring body and enable the angle of the pin to be adjusted, at least portions of the halo ring body are circular in cross-section, and preferably the body is circular in cross-section throughout its length. This enables the circular opening of the pin clamp to engage about the circular body, while permitting it to slide along the body into selected adjusted positions. It will be appreciated that the circular cross-section of the halo ring body need not be for its entire length. It may only be along the sides and/or front of the halo ring body in the general vicinity of the anticipated locations of the pins.

Additionally, at least a pair of attachment clamps may be secured similarly to the halo ring body at adjusted meridian positions along the body and at adjusted angular orientation relative to the body. An attachment bolt may be passed through a superstructure clamp for securing a superstructure clamp to the attachment clamp and simultaneously securing the attachment clamp to the halo ring body. The superstructure clamp is used to couple the halo ring to a support system, for example, a halo vest as described and illustrated, for example, in U.S. Pat. Nos. 5,121,741 and 5,261,873. With the foregoing construction, the pin clamps and attachment clamps can be located virtually anywhere along the arc of the halo ring body and in any angular orientation relative to the body.

In a preferred embodiment according to the present invention, there is provided a halo comprising an elongated halo body shaped to generally extend about at least a major portion of the periphery of an individual's head and to lie in laterally spaced relation thereto, a pair of pin clamps slidable and movable into selected positions along the halo body, retention elements cooperable between the pin clamps and the halo body for at least temporarily retaining the pin clamps along the body in selected positions and a pin carried by each clamp for securing the halo and the individual's head to one another.

In a further preferred embodiment according to the present invention, there is provided a halo comprising an elongated halo body shaped to generally extend about at least a portion of the periphery of an individual's head and lying in a plane, at least portions of the halo body along opposite sides thereof having circular cross-sections, a pair of pin clamps disposed in respective circular portions of the halo body and rotatable about axes lying generally in the plane of the body into selected angular positions about the body and a pin carried by each clamp for securing the halo body and the individual's head to one another with the pins in selected angular positions about the body and relative to the individual's head.

Accordingly, it is a primary object of the present invention to provide a novel and improved halo ring for use by patient's with cervical or spinal injuries for immobilizing the neck of the patient to promote healing wherein the pins attaching the halo ring to the patient's skull, as well as the structure connecting the halo ring and the support system for the halo ring are substantially infinitely adjustable along the halo ring and in angular orientation about the halo ring.

BEST MODE FOR CARRYING OUT THE INVENTION

Figure 1:
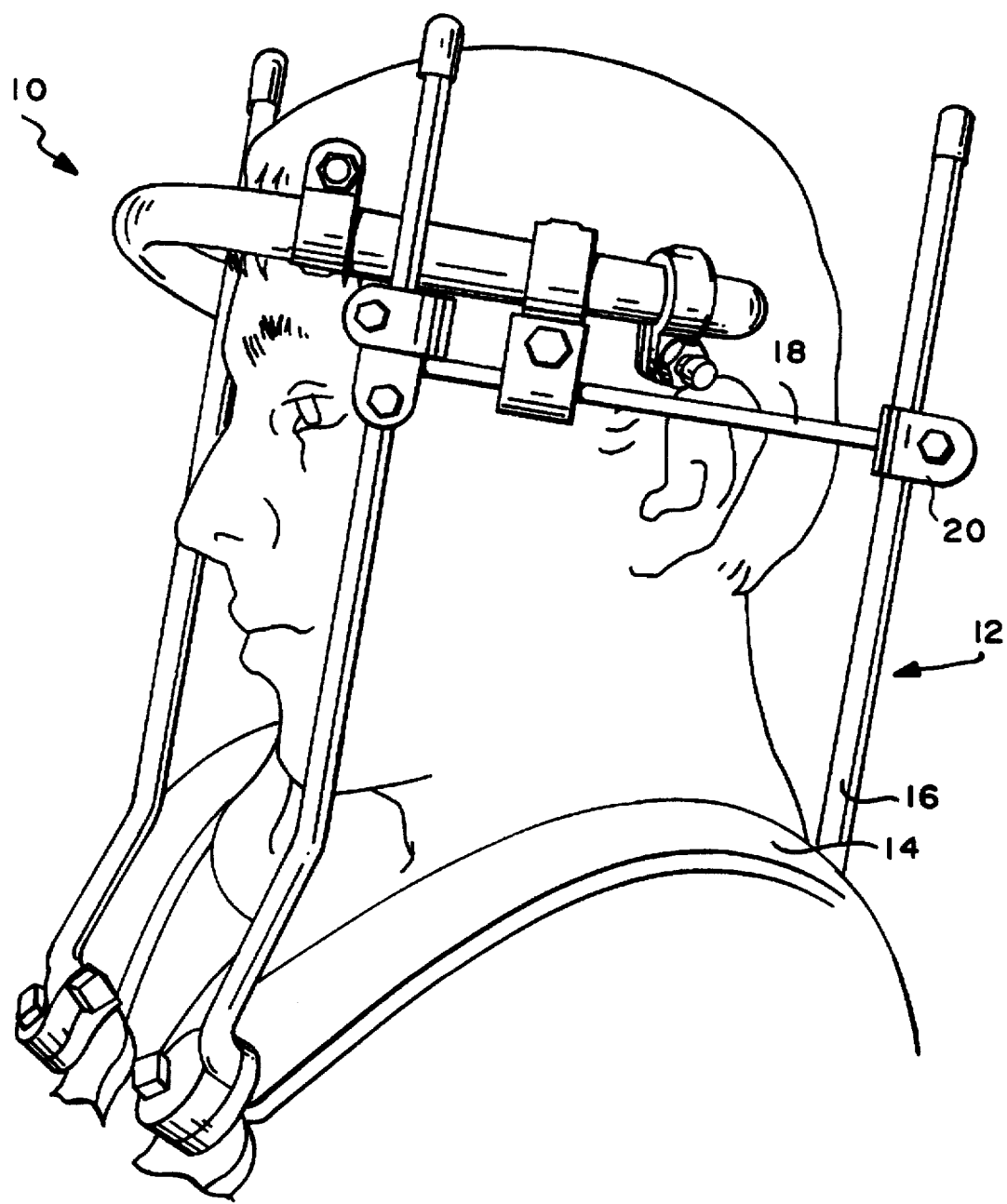
FIG. 1 is a perspective view of a halo ring constructed in accordance with the present invention and illustrated attached to a support structure worn by an individual.

Referring now to the drawings, particularly to FIG. 1, there is illustrated a halo system which includes a halo ring, generally designated 10, mounted on a support structure 12, in turn mounted on a halo vest 14. Vest 14 is typically secured to the torso of the individual wearing the halo system and provides a body support for the supporting structure 12 for the halo ring 10 and the individual's head. The support structure 12 includes a plurality of vertically extending rods 16 to which side cross rods 18 are adjustably secured by suitable clamps 20. The side rods 18 form the supporting structure for the halo ring 10. It will be appreciated that various types of halo vests, as well as supporting structure can be provided for use with the halo ring of the present invention and form no part of the present invention.

Figure 2:
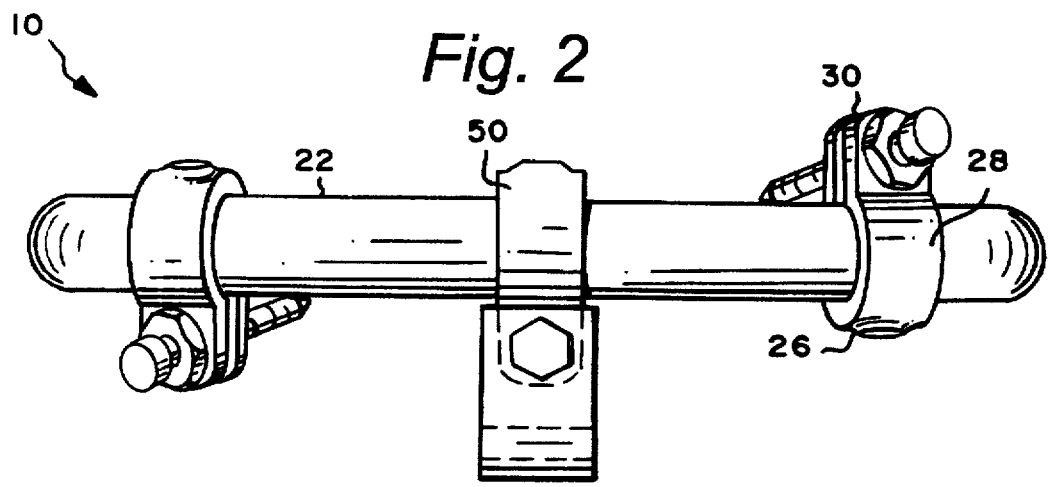
FIG. 2 is a side elevational view of the halo ring.
Figure 3:
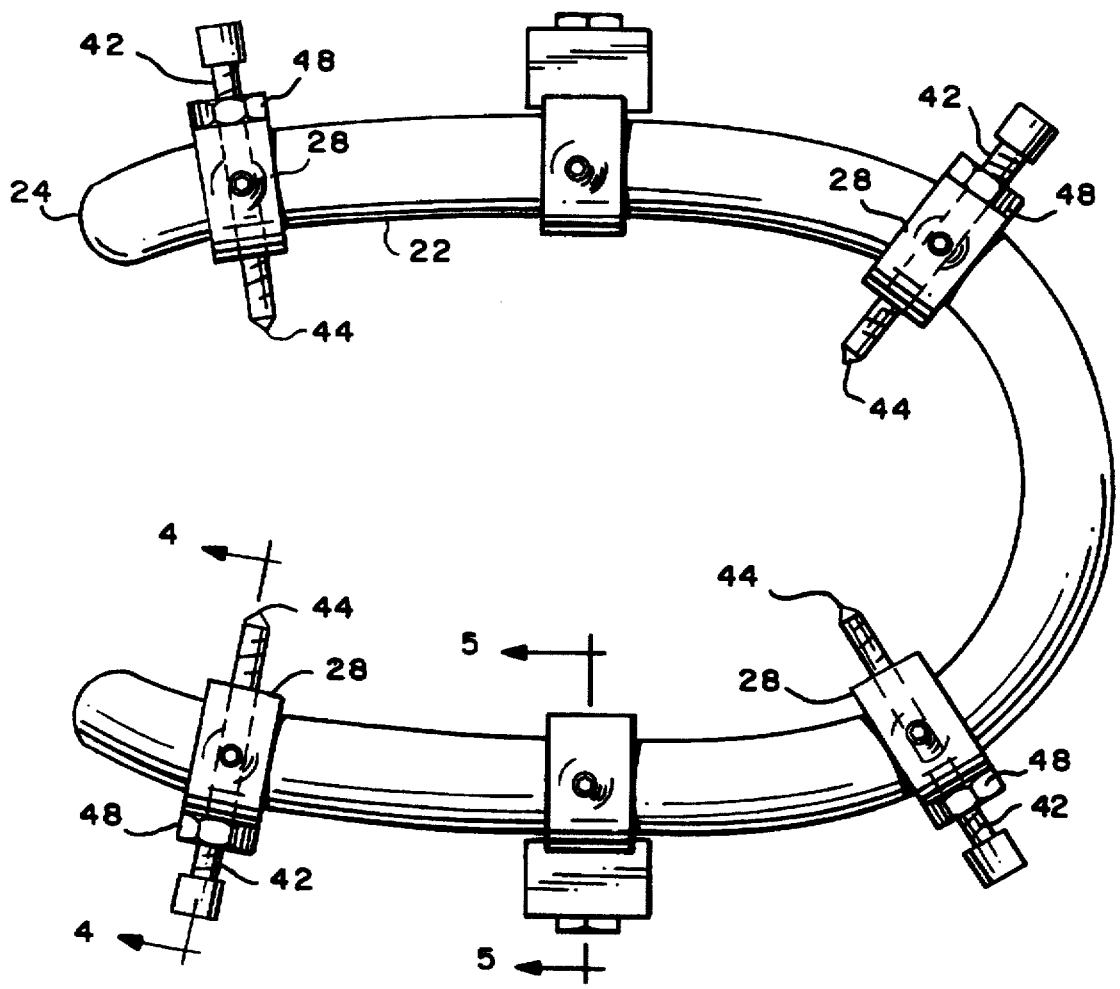
FIG. 3 is a top plan view of the halo ring.
Figure 4:
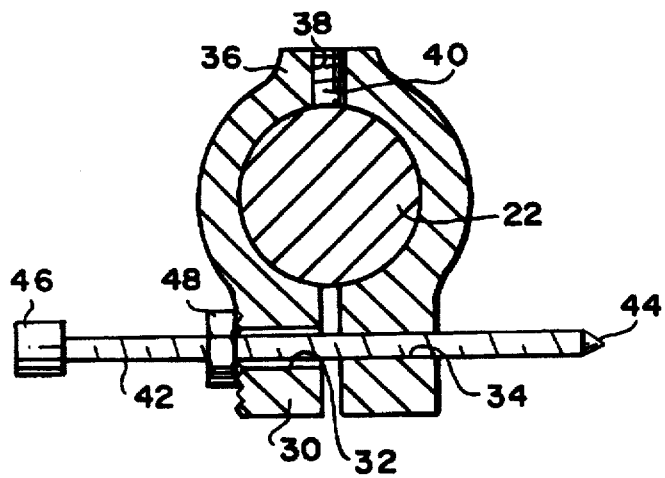
FIG. 4 is a cross-sectional view taken generally about on line 4—4 in FIG. 3.
Figure 5:
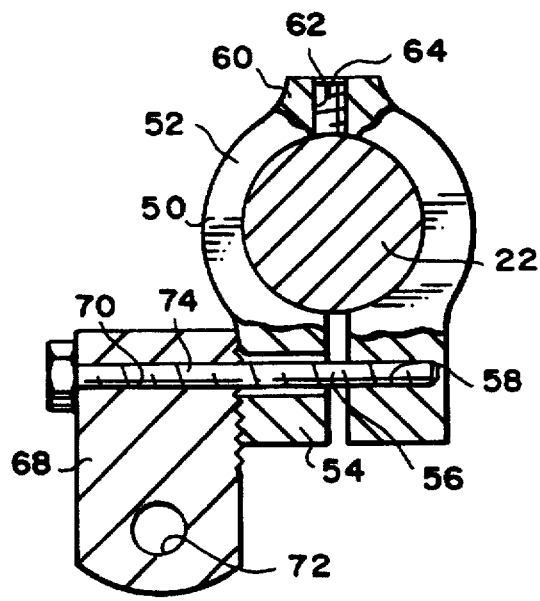
FIG. 5 is a cross-sectional view taken generally about on line 5—5 in FIG. 3.

Referring now to FIGS. 2 and 3, the halo ring 10 includes an elongated halo body 22 shaped to generally extend about and to lie in spaced relation to at least a major portion of the periphery of an individual's head. While the ring 22 may have different shapes in plan view than as illustrated in FIG. 3, ring 22 is preferably elliptical in shape, with one end of the ellipse removed. Thus, the distal ends 24 of the halo ring 22 terminate in spaced relation to one another. Additional shapes in plan view such as an interrupted circular shape or shapes corresponding to a specific contour of an individual's head may be used. The halo ring body 22 is preferably formed of a material which will permit taking X-rays. For example, the body 22 may be formed of a non-ferrous hollow metal tube or a non-ferrous solid metal tube. Additionally, the body 22 may be formed of a hollow or solid plastic material. Importantly, as illustrated in FIGS. 4 and 5, the halo ring body 22 is circular in cross-section such that pin and attachment clamps may be disposed at longitudinally and angularly adjusted positions thereabout as described hereinafter. Also, as seen in FIG. 2, the halo ring body 22 preferably lies in a single plane.

A plurality of pin clamps are disposed on the halo ring. The pin clamps 26 generally comprise a split ring 28 terminating at adjacent opposite ends in enlarged flanges 30. The split ring, as illustrated in FIG. 4, is slidable onto an end 24 of the body 22 and along the body 22 into a longitudinally adjusted position. The enlarged flanges 30 have registering openings 32 and 34. Opening 32 comprises a smooth borehole, while opening 34 is tapped. Additionally, opposite the flanges 30 on ring 28 is a boss 36 which has a tapped aperture 38 for receiving a retention element, e.g., a set screw 40.

Each pin clamp 26 is provided with a threaded pin 42. Pin 42 terminates in a pointed end 44 for engaging the individual's skull and has a head 46 at its opposite end. A lock nut 48 is also provided on pin 42. It will be appreciated that the pin 42 may be inserted through the bore 32 and threaded along tapped opening 34 for engagement with the individual's skull. By threading lock nut 48 into engagement with a flange 30, the pin 42 can be locked in position. Additionally, the flanges 30 may be displaced toward one another by threading the lock nut 48 to tighten the pin clamp 26 about the halo body 22 during installation, as particularly described hereinafter. The set screw 40 is used as described hereafter to temporarily retain the pin clamp in an adjusted longitudinal and angular position along the halo body 22 as described below.

To secure the halo ring to the support structure 12, an attachment clamp 50 is provided. The attachment clamp 50 is similar in construction to the pin clamp 26 and comprises a split ring 52 having enlarged flanges 54 at adjacent ends. Flanges 54 include a smooth bore 56 and a tapped opening 58 in registry one with the other. A boss 60 is provided along the opposite side of the attachment clamp 50. A tapped hole 62 is provided in boss 60 for receiving a threaded set screw 64. For attaching the attachment clamp 50 to the horizontal support rod 18, a securing element 68 is provided which has a smooth bore aperture 70 through its upper end and smooth bore aperture 72 orthogonally related thereto for receiving the side support rod 18. The element 68 may have a set screw for securing the element 68 in an adjusted position along the side rod 18. The bolt 74 passes through the bore 70 of element 68 and the bore 56 of flange 54 for threaded engagement in the tapped bore 58 of the opposite flange of the attachment clamp 50. Thus, by threading the bolt, the attachment clamp 50 is secured about the halo body 22, securing the element 68 to the attachment clamp. Serrated edges may be provided between the flange 54 of the attachment clamp 50 and the element 68 to enhance the securement.

In using the halo ring of the present invention, a first pair of pin clamps are disposed on the halo body 22 by placing the split clamp rings in their open condition about body 22 and sliding them to a front location. The attachment clamps 50 are then similarly inserted on opposite sides of the ring, followed by the final pair of pin clamps, also inserted on opposite sides of the ring. The attachment clamps are coupled to the side support rods and secured, positioning the halo ring body 22 about the patient's head. Each of the pin clamps 26 may then be slidably adjusted along the length of the halo body to a selected position. Additionally, because the pin clamps are in split ring form, the clamps per se can be adjusted angularly about the body 22. Once the longitudinal and angular positions of the pins of the pin clamps are selected, the set screws 40 are threaded down to temporarily secure the pin clamps in their selected angular and longitudinal positions relative to the halo ring body 22. The pins 42 are then threaded to engage the skull. When threaded sufficiently, the lock nuts 48 are tightened up against the remote flange of the pin clamps. By tightening lock nuts 48, the pin clamps are tightened about the halo body 22, as well as prevented from unthreading from the pin clamp.

Figure 6:
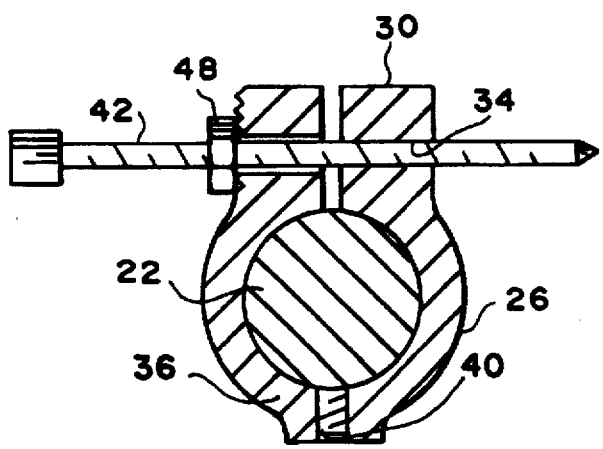
FIG. 6 is a view similar to FIG. 4 illustrating the pin clamp above the equator of the halo ring.

Referring to FIGS. 1 and 6, it will be appreciated that the pins of the pin clamps can be disposed above the halo ring, i.e., above the centerline or equator of the halo ring body 22. To accomplish this, the pin clamp is applied to the ring in a reverse manner, i.e., it is rotated 180° about an axis normal to both the pin and halo ring opening axes and then inserted about the ring. In this manner, the flanges 30 are located above the ring. With the pin threaded through the flange located proximal to the individual's head, the above equator pin clamp can be secured to the skull and to the halo ring similarly as described above. It will be appreciated that one or more or all of the pin clamps can be located above or below the halo ring.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A halo comprising:
   an elongated halo body shaped to generally extend about at least a major portion of the periphery of an individual's head and to lie in laterally spaced relation thereto;
   a pair of pin clamps slidable and movable into selected longitudinal positions along said halo body;
   retention elements cooperable between said pin clamps and said halo body for at least temporarily retaining said pin clamps along said body in said selected positions;
   said halo body being interrupted and terminating in opposite ends spaced one from the other, said pin clamps being slidably received over at least one end of and along said body for location in said selected positions along said body;
   a pin carried by each clamp for securing the halo and the individual's head to one another;
   at least portions of said halo body being circular in cross-section, said pin clamps being disposed about said circular body portions and rotatable thereabout into selected angular positions for selectively adjusting the angular orientation of the pins relative to the halo body and the individual's head;
   said retention elements being cooperable between said pin clamps and said body to at least temporarily retain said pin clamps in said selected angularly adjusted orientations about said body, thereby at least temporarily establishing the angular orientation of the pins.

2. A halo according to claim 1 including a pair of generally c-shaped attachment clamps for securing said halo body to a halo support, said attachment clamps substantially encompassing and being slidable along said halo body for movement into selected positions along said body, retention elements cooperable between said attachment clamps and said halo body for at least temporarily retaining said attachment clamps along said body in said selected positions and an attachment bolt received in each attachment clamp for securing said attachment clamp to the halo support.

3. A halo according to claim 1 wherein each of said pin clamps includes a split ring having flanges at adjacent ends, said pin received in said flanges of said pin clamp for securing said pin clamp in said selected position along said body.

4. A halo according to claim 1 wherein said halo body comprises a non-ferrous hollow metal tube.

5. A halo according to claim 1 wherein said halo body comprises a hollow tube formed of plastic material.

6. A halo according to claim 1 wherein said halo body comprises a solid rod of plastic material.

7. A halo according to claim 1 wherein said halo body comprises a solid rod of metal material.

8. A halo according to claim 1 wherein said halo body comprises a tube.

9. A halo according to claim 1, wherein said halo body is circular in cross-section throughout its length and is interrupted to terminate in opposite ends spaced one from the other, said pin clamps being slidably received over at least one end of and along said body for location in said selected positions, and further comprising a pair of attachment clamps for securing said halo body to a halo support, said attachment clamps being slidable along said halo body for movement into selected positions along said body, retention elements cooperable between said attachment clamps and said halo body for at least temporarily retaining said attachment clamps along said body in said selected positions and an attachment bolt received in each attachment clamp for securing said attachment clamp to the halo support.

10. A halo according to claim 9 wherein said pin clamps and said attachment clamps each include a split ring having flanges at adjacent ends, said pins being received in said adjacent flanges of each said pin clamp for securing said pin clamps in said selected longitudinal positions and angular orientations along said body, said attachment clamps being rotatable about said halo body into selected angular positions for selectively adjusting the angular orientation of the attachment clamps relative to the halo support, said bolts being received in said adjacent flanges of said attachment clamps for securing said attachment clamps in selected longitudinal positions and angular orientations along said body.

11. A halo according to claim 10 wherein said halo body has a generally elliptical configuration and lies in a plane.

12. A halo comprising:
   an elongated halo body shaped to generally extend about at least a portion of the periphery of an individual's head and lying in a plane;
   at least portions of said halo body along opposite sides thereof having circular cross-sections;
   a pair of pin clamps disposed in respective circular portions of said halo body and rotatable about axes lying generally in the plane of said body into selected angular positions about said body; and
   a pin carried by each clamp for securing the halo body and the individual's head to one another with the pins in selected angular positions about said body and relative to the individual's head;
   said halo body being interrupted and terminating at opposite ends spaced one from the other;
   said pin clamps being slidably received over at least one end of and longitudinally along said circular body portions into selected longitudinal positions for selectively adjusting the longitudinal location of the pins along the halo body and the individual's head; and
   a pair of attachment clamps for securing said halo body to a halo support, said attachment clamps being slidable along said halo body for movement into selected positions along said body, said attachment clamps being disposed about said circular body portions and rotatable thereabout into selected angular positions for selectively adjusting the angular orientation of the attachment clamps about the halo body.

13. A halo according to claim 12 including a pair of attachment clamps for securing said halo body to a halo support, said attachment clamps being slidable along said halo body for movement into selected positions along said body, and an attachment bolt received in each attachment clamp for securing said attachment clamp to the halo support.

14. A halo according to claim 12 wherein said halo body comprises a solid rod of plastic material.

15. A halo according to claim 12 wherein said halo body comprises a solid rod of metal material.

16. A halo according to claim 12 wherein said halo body comprises a tube.

* * * * *